United States Patent [19]

Shah

[11] Patent Number: 5,128,240
[45] Date of Patent: Jul. 7, 1992

[54] IMMUNOLOGICAL METHOD OF MEASURING UNSTABLE ANALYTES USING CROSS-REACTIVE ANTIBODIES

[75] Inventor: Vipin D. Shah, Saratoga, Calif.

[73] Assignee: International Immunoassay Laboratories, Inc., Santa Clara, Calif.

[21] Appl. No.: 296,542

[22] Filed: Jan. 12, 1989

Related U.S. Application Data

[63] Continuation of Ser. No. 87,415, Aug. 20, 1987, abandoned, which is a continuation of Ser. No. 684,341, Dec. 20, 1984, abandoned.

[51] Int. Cl.⁵ ................ G01N 33/531; G01N 33/532; G01N 33/53; G01N 33/543
[52] U.S. Cl. .................... 435/7.1; 436/501; 436/518; 436/536; 436/543; 436/544; 436/815; 436/822; 436/824; 436/825; 435/7.9; 435/961
[58] Field of Search ............... 436/501, 518, 536, 543, 436/544, 815, 822, 824, 825

[56] References Cited

U.S. PATENT DOCUMENTS 4,243,749  1/1981  Sadeh et al. .................... 436/805 X
4,288,538  9/1981  Groman et al. .................. 435/52 X
4,347,312  8/1982  Brown et al. .................... 435/7

OTHER PUBLICATIONS

Isetta, A. et al., Eur. Journ. Immunol, 6: 737–742 (1976).

Primary Examiner—Esther L. Kepplinger
Assistant Examiner—Toni Scheiner
Attorney, Agent, or Firm—Skjerven, Morrill, MacPherson, Franklin & Friel

[57] ABSTRACT

A quantitative immunoassay for a beta-lactam antibiotic in a sample, which may contain open and closed ring forms of the antibiotic, is disclosed. Closed-ring forms of the antibiotic in the sample are converted to open-ring protein conjugates and detected through immunospecific reaction with antibodies raised against the open-ring protein conjugate form of the beta-lactam antibiotic.

18 Claims, 2 Drawing Sheets

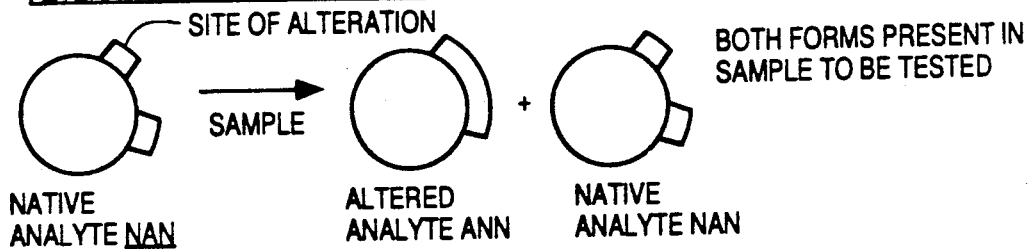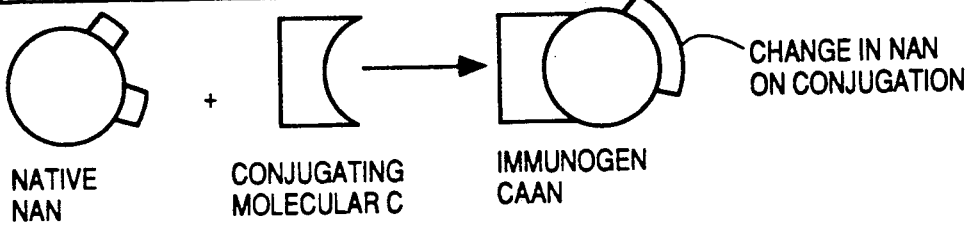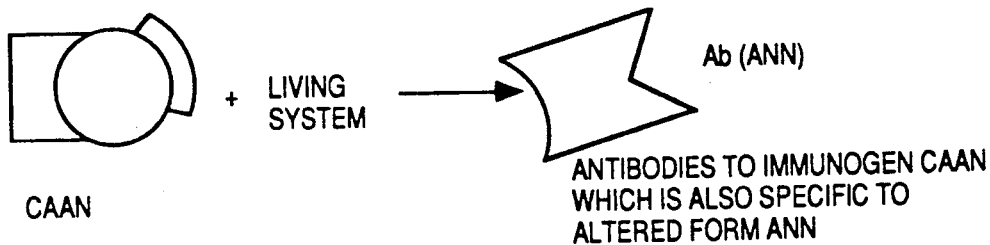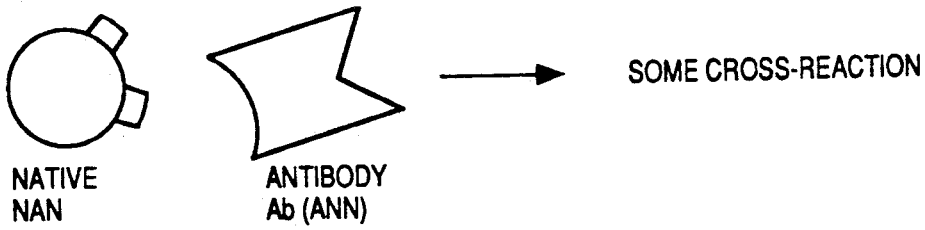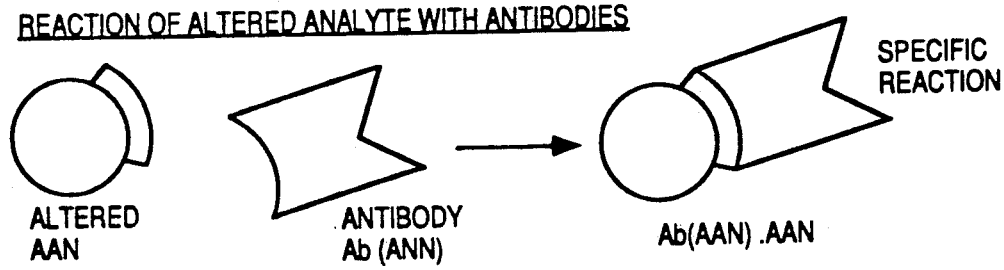
Fig._1.

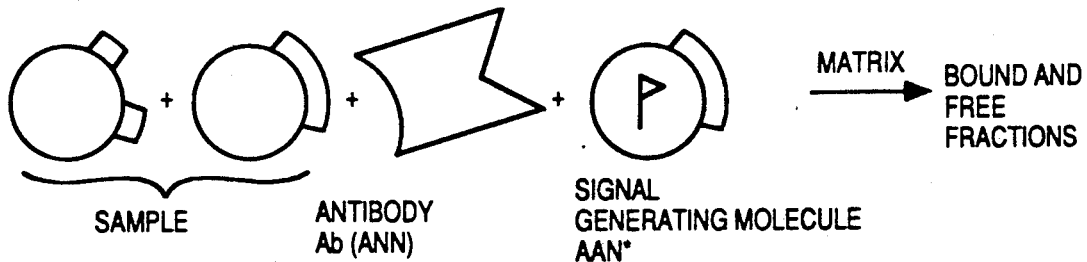
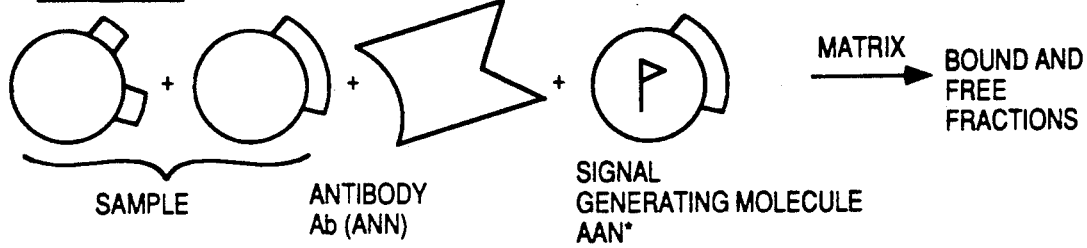
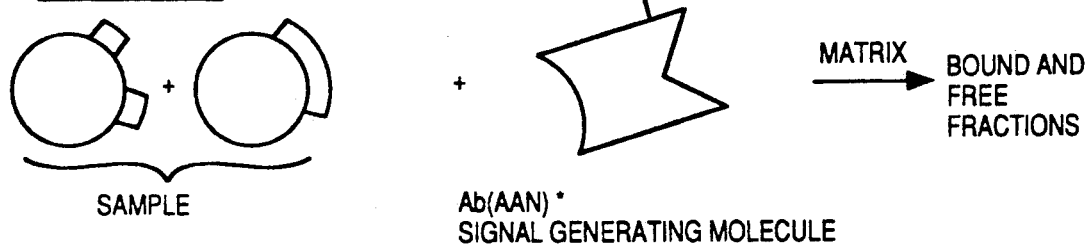
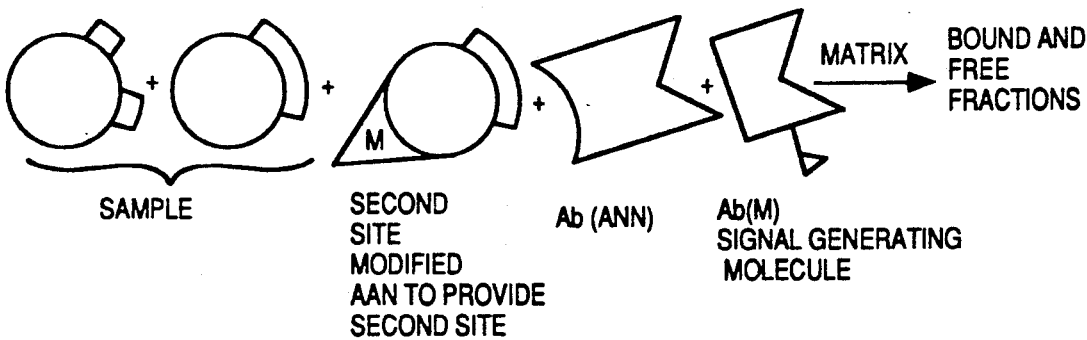
Fig._2.

IMMUNOLOGICAL METHOD OF MEASURING UNSTABLE ANALYTES USING CROSS-REACTIVE ANTIBODIES

This application is a continuation of Ser. No. 07/087,415, filed on Aug. 20, 1987, now abandoned, which is a continuation of Ser. No. 06/684341, filed on Dec. 20, 1984, now abandoned.

BACKGROUND OF THE INVENTION

1. Field of the Invention

The present invention relates generally to immunological assay techniques for determining the presence of an analyte in fluids and particularly to an immunoassay testing method utilizing cross-reactive antibodies which has particular application in the qualitative and quantitative determination of the level of unstable analytes such as beta-lactam antibiotics in fluids with particular emphasis on penicillin detection and measurement.

2. Description of Prior Art

Immunoassay methods are extensively described in literature, for example as in Methods in Enzymology, Vol. 92, Pages 377–543, (1983) Academic Press, New York. Generally, immunoassay methods require (i) specific antibodies raised against the analyte of interest, and (ii) a signal generating molecule which is either derived from the analyte of interest or from the antibody raised specifically to the analyte of interest, or another molecule which reacts with the said antigen or antibody. The antibody, the analyte of interest and the signal generating molecule may be reacted in one-phase or two-phase systems. Thereafter, the amount of signal generating molecules that are bound directly or indirectly to the specific antibody are differentiated from the unbound signal generating molecule. The proportion of bound or free molecule gives a measure of analyte present in the sample.

Several patents have been issued covering the use of various signal generating molecules (flourescence, enzyme, radioisotope, latex agglutination etc.) various techniques of conducting the assay, and ways of immobilizing antibodies.

The prior art has generally recognized and demanded that an accurate measurement technique must utilize an antibody that is specific to the analyte being measured. Such specific antibodies are raised by injecting in a living system capable of forming antibodies, A. highly purified analyte B. highly purified analyte conjugated to a high molecular weight substance, or, C. a highly purified fragment of the analyte of interest as such or as a conjugated molecule The living system responds to this "invasion" of a foreign molecule and produces specific antibodies to the analyte of interest.

In practice, one often forms cross-reacting antibodies which not only partly react to the analyte of interest but also react with other constituents which may be commonly present in the sample to be assayed. These cross-reactive antibodies may interfere in the test procedure and prevent specific measurement of the analyte. It is because of this that the prior art has generally required the use of specific antibodies.

The prior art also describes ways of minimizing the harmful effect of cross-reactive antibodies. This could be achieve by the purification of antibodies by affinity chromatography, the use of hybridoma techniques to make specific antibodies or the use of so called "sandwich" techniques. The "sandwich" approach relies on redundancy to eliminate harmful effects of cross-reactive antibodies. Thus for example, specific antibodies are raised against the analyte in two different living systems. In the actual test, the analyte is sandwiched between these two different but specific antibodies. If the cross-reactivity was resulting from the living system used to make the antibody, such an approach will eliminate cross-reactivity.

Another common "sandwich" technique involves making two pure fragments of the analyte and making specific antibodies against each fragment. In the actual assay, the intact analyte is sandwiched between the antibodies made against its fragments. Such an approach will eliminate cross-reactivity problems which occur due to the presence of antibodies against a portion of the analyte.

Such immunological techniques utilizing specific antibodies are not feasible in many situations, including the following:

(a) When the analyte could not be obtained in a pure enough form and hence specific antibodies could not be raised against it. Many delicate biochemicals undergo changes as they are purified and fall into this category.

(b) When the analyte is a sensitive hapten which could not be conjugated without altering the analyte. Beta-lactam antibiotics for example react very easily with proteins. One often needs to form a conjugate of beta-lactam antibiotics with a protein to render it immunogenic. However, the beta-lactam ring is opened during such conjugation and antibodies so raised will only cross-react with the intact antibiotic molecule and are not specific to the native antibiotic molecule.

(c) When the analyte could be obtained in a pure form and specific antibodies could be raised. However, the sample in which such analyte is commonly found usually contains other molecules which are so similar to the analyte that the antibody would cross-react with them. Such a problem is commonly encountered in immunologically measuring isoenzymes. Antibodies specifically raised against one isoenzyme cross-react with many other isoenzymes concurrently present in the sample. Such a problem prevents measurement of the CK-MB isoenzyme by using antibodies raised specifically against it, since such antibodies will cross-react with CK-MM and CK-BB isoenzymes.

A novel method of specifically measuring an analyte which falls into Category c above has been disclosed in a co-pending patent application, Two-Site Cross-reaction Immunometric Sandwich Assay Method, Ser. No. 165,001, filed Jun. 30, 1980. The difference in the prior art and that pending application is that the invention of that patent application requires the use of cross-reactive rather than specific antibodies. The combination of cross-reactive antibodies and adaptation of "sandwich" techniques allows one to specifically measure analytes which herebefore were not specifically measurable by immunological techniques in which specific antibodies were used. Another co-pending patent application. Ser. No. 597,593, Matrix Aided Immunometric Assay for CK-MB, describes the use of a novel matrix to enhance the speed and accuracy of such a test procedure. Yet another application, Two-Site Enzyme Labeled Cross-Reaction Immunometric Sandwich Assay Method, Ser. No. 635,893, filed Jul. 30, 1984 (a CIP of Ser. No. 165,000) describes the use of an enzyme label.

The prior art fails to disclose methods of using cross-reactive antibodies to measure analytes which fall in the Categories a and b above. In the case of Category b, the analyte is reactive and changes from its native analyte form (NAN) to an altered analyte form (abbreviated as AAN) when conjugated for immunization. The antibody thus formed is not specific to the native analyte NAN; however, the antibody would have some cross-reactivity to that molecule. Since such analytes are very reactive, they lend themselves to easy alteration. Thus, a sample containing the analyte of interest often contains both the native (NAN) and altered (AAN) forms of the analyte, and the antibody would react with differing intensities with both forms and would not be suitable for measuring these forms.

Roberts et al. (Lancet, Vol. II, Pages 319-321, August 1977) have described the use of cross-reactive antibodies. They use antibodies raised against CK-BB (creatine kinase, BB isomer) to measure CK-MB (creatine kinase, MB isomer). Antibodies to CK-BB are not raised against CK-MB, they cross-react with CK-MB. The difference between teachings of Roberts and the present invention lies in the fact that two analytes, for example CK-BB and CK-MB, one specific to the antibody and one cross-reactive with the antibody are left unaltered by Roberts and both of them are measured. However, because both analytes do not react similarly, the accuracy of quantitation is affected by the relative proportions of each analyte. In the present invention advantage is taken of the relative instability of the analyte of interest to alter it prior to or during the immunoassay procedure so that it is made specific to the cross-reactive antibody. The cross-reactive antibody is thus made useful instead of being a nuisance and since both forms are converted into one form, quantitation is accurate. This is achieved by creating a matrix in which the native analyte of interest is altered rapidly and thus made specific to the antibody that was formed. The novel feature of this invention is that the antibody is not purified but that the analyte is changed to make it specifically reactive to the cross-reactive antibody.

One specific utility of this novel approach is for the detection of allergy causing antibiotics contamination. The utility of this invention is demonstrated through the detection of penicillin contamination in milk. However, the teaching of this invention is applicable to all beta-lactam antibiotics. The present invention could be used for a relatively simple and inexpensive method for detecting the presence of similar beta-lactam antibiotics in other products.

Products contaminated with beta-lactam antibiotics cause allergenic reactions in some individuals. Also, the presence of such compounds may make it impossible to use such a product for its ultimate use. For example, milk contaminated with penicillin may not be suitable for manufacture of cultured cheese products.

Present methods for detecting antibiotics generally require microbial assays and, hence, considerable time and laboratory facilities are necessary. Present chemical tests do not have sufficient sensitivity to detect the minimum tolerable levels of antibiotic concentration.

It is known that the beta-lactam ring of penicillin and other such antibiotics is very reactive. Thus, the native penicillin may undergo changes, particularly through opening of the beta-lactam ring. Such conversion depends upon the environmental conditions such as pH, temperature, presence of sugars, proteins etc. to which the antibiotic is exposed. Thus, the degree of conversion may be different when it is injected into animals to treat infection, from when it is present in milk or from when it is present in fermentation broth.

While immunological methods for detecting penicillin and similar antibiotics have been described in prior art such as U.S. Pat. No. 4,347,312, or in commercial products such as the SPOT test from Angenics (100 Inman Street, Cambridge MA 02139), they do not teach easy-to-use immunological methods capable of measuring the antibiotic which may be present in both the open beta-lactam ring (e.g. penicilloyl form) and closed beta-lactam ring structure (e.g. native penicillin).

It is well accepted that the open beta-lactam ring form (e.g. penicilloyl group) is the key determinant in antibiotic allergy. Antibodies used to immunologically measure antibiotics (e.g. penicillin) such as that described in U.S. Pat. No. 4,347,312, are usually formed in such a way that they are specific to the open beta-lactam ring (e.g. penicilloyl group) rather than native molecule (e.g. penicillin). Authors such as Kitagawa et al., A New Method for Preparation of an Antiserum to Penicillin and Its Application for Novel Enzyme Immunoassay of Penicillin, Journal of Biochemistry, Volume 84, Page 491, 1978, have recognized this and have developed methods for producing antibodies specific for the native molecule. Jean-Michel Wal et al., Radioimmunoassay of Penicilloyl Groups in Biological Fluids, FEBS Letters, Volume 57 (1), Page 9, 1978, and Anna Moer Isetta et al., Affinity and Specificity of Penicillin-Antibody Interaction Determined by an Enzyme Immunoassay, Eur. Journal of Immunology, Volume 6, Page 737, 1976 on the other hand described methods of producing antibodies against the open beta-lactam ring derivative. Thus, the prior art describes methods for immunologically measuring either the open beta lactam ring (e.g. penicilloyl derivatives) or the closed beta-lactam ring (e.g. penicillin) but not both forms simultaneously.

The opening of the beta-lactam ring causes the antibiotic (e.g. penicillin) molecule to loose its antibacterial activity. Thus, conventional microbiological methods measure native antibiotics (e.g. penicillin) rather than the open beta-lactam ring (e.g. penicilloyl) derivatives. The native antibiotic (e.g. penicillin) still has a very reactive beta-lactam ring and is capable of forming allergenic antigens when it could combine with other molecules to form open beta-lactam derivatives. Thus, microbiological methods for measuring antibiotics contamination give only a partial and an indirect measure of allergenicity of such products.

The allergic reaction in humans, which could be caused by food or drug products contaminated with penicillin or other beta-lactam antibiotics, may result from both native form as well as the altered derivatives. This is because the human body will convert some of the native antibiotic into allergenic derivatives in-vivo. It would be useful therefore to simultaneously measure both the altered form which is allergenic and the intact form which has potential allergenicity. However, the prior art does not describe a method capable of measuring simultaneously both forms of antibiotics, namely those containing an intact beta-lactam ring and those containing open beta-lactam ring derivatives.

The present invention provides means of immunologically measuring both the closed ring antibiotics and the open beta-lactam ring derivative. This is achieved by converting the closed ring antibiotic molecule in the sample into its open beta-lactam ring form. Such a measurement of both forms would provide a more reliable estimate of allergenicity of penicillin and similar beta-lactam ring antibiotics when present as contaminants in foods and drugs.

SUMMARY OF THE INVENTION

It is an object of the present invention to use cross-reactive antibodies to measure a reactive analyte such as an antibiotic molecule containing a beta-lactam ring, wherein the structural change in the analyte when the analyte is exposed to its commonly found environment is similar to the immunogenic form achieved through conjugation for production of antibodies.

It is another object of the present invention to simultaneously measure both "native" hapten and its "altered" form found in the sample through the use of an antibody which is cross-reactive to the "native" analyte but is specific to the "altered" form.

It is a further object of the present invention to simultaneously measure "native" and "altered" analyte particularly antibiotics containing a beta-lactam ring by providing a reaction matrix in which the native form is rapidly changed to the altered form and measurement conducted.

It is yet another object of the present invention to describe the composition of reagents to allow rapid immunological measurement of the beta-lactam antibiotics in which both the native antibiotic and its altered version namely, open beta-lactam ring derivatives are reacted with an antibody under conditions in which the closed beta-lactam ring of the native antibiotic is opened during the reaction.

It is yet a further object of the present invention to describe a test kit which could be used to measure very low concentrations of closed beta-lactam ring antibiotics and their open beta-lactam ring derivatives rapidly.

The test method of the present invention is useful when the analyte of interest in a sample exists in two related molecular structures and it is desired to measure all of the analyte, regardless of structure. The method includes utilizing an antibody which is cross-reactive with one structure and specific to the other structure. To practice the test method, the analyte of the cross-reactive structure is converted through conjugation such that the form of the analyte structure which is specific to the antibody is created in the test sample. The actual procedure may utilize competitive, sequential immunological or sandwich techniques and be conducted with a variety of tags.

The test is particularly suited for beta-lactam ring antibiotics which may exist in either open ring or closed ring molecular structures. The practiced test procedure converts all molecular structures to open ring structures and uses a RIA tagged antibody. Particular examples describe a test procedure for measuring penicillin contaminants in milk.

These and other objects and advantages of the present invention will no doubt become apparent to those of ordinary skill in the art after having read the following detailed description of the preferred embodiments which are illustrated in the several figures of the drawing.

IN THE DRAWINGS

FIG. 1 depicts various reactions between native analytes, altered analytes and the cross-reactive antibodies.

FIG. 2 and the accompanying description depicts various immunoassay techniques that may be used with the present invention.

DESCRIPTION OF THE PREFERRED EMBODIMENT

The present invention teaches a novel method of using cross-reactive antibodies to immunologically measure a native analyte (NAN), where such native analyte (NAN) (i) also typically exists in an altered analyte (AAN) form in the sample environment in which it is commonly found, and (ii) the altered (AAN) form of such analyte is immunologically distinct from its native (NAN) form, and (iii) the AAN form is immunologically similar or identical to immunogens (abbreviated as CAAN) prepared from the NAN analyte, and (iv) the NAN analyte can be converted to its AAN form in a reaction matrix which enhances the conversion of the NAN analyte to its AAN form.

The present invention with reference to FIGS. 1 and 2 includes the following steps:

a. Render the native analyte (NAN) of interest into an immunogenic form (CAAN) which is immunologically similar or identical to the altered (AAN) form in which the analyte is partially present in the sample to be assayed.

b. Prepare antibodies Ab[AAN] against the immunogenic form (CAAN) which will specifically react with the altered form (AAN) of the native analyte (NAN). However, Ab[AAN] is only cross-reactive with NAN.

c. Conduct the immunological reaction among samples containing "native" and "altered" analyte and antibodies defined in b above and a signal generating molecule in a reaction matrix in which the "native" form of the analyte is rapidly changed to its "altered" AAN form (FIG. 2).

d. Separate bound signal generating molecule from free signal generating molecule. Determine the extent of reaction and hence concentration (or presence) of NAN plus AAN from a proportion of free or bound signal generating molecule.

A differing reaction matrix should be utilized to optimize results for each analyte. Such a matrix will be optimized to convert NAN to AAN and in most cases will be different from that used when one measures NAN directly by using antibodies specific to NAN.

Thus, a novel feature of this invention is the use of cross-reactive antibodies and appropriate reaction matrix which allow one to simultaneously measure NAN and AAN immunologically. Such immunological measurement of NAN and AAN is not feasible with antibodies specific to NAN and in a matrix commonly used with specific antibodies.

FIGS. 1 and 2 depict the concepts described above.

NOMENCLATURE

NAN—Native Analyte
AAN—Altered Analyte
Ab (AAN)—Antibody reactive with altered analyte
AAN*—Signal generating molecule derived from AAN
Ab (AAN)*—Signal generating molecule from antibody to AAN
MAAN—Molecule capable of reacting with Ab (AAN) on one side and Ab (M) on the other side.
M—Modifier of AAN

REPRESENTATION OF VARIOUS IMMUNOASSAY TECHNIQUES

1. Competitive reaction (See FIG. 2a) in which sample is reacted simultaneously with cross-reactive antibodies and signal generating molecule made from altered analyte.

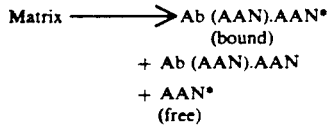

2. Sequential reaction (See FIG. 2b) in which sample is reacted with cross-reactive antibodies and then signal generating molecule made from altered analyte.

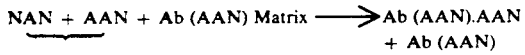

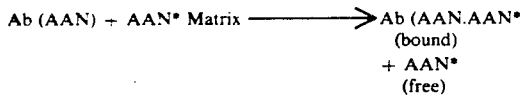

3. Immunometric reaction (See FIG. 2c) in which signal generating molecule is made from cross-reactive antibodies.

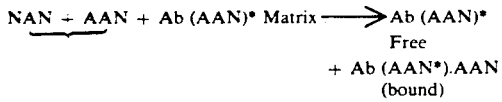

4. Two-Site Immunometric reaction (See FIG. 2d) in which a second site M is created by using a competitive reaction followed by the use of signal generating molecule made from antibodies to M.

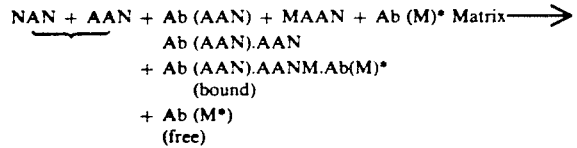

These concepts are depicted in FIG. 2.

The obvious extension of this invention will involve separate estimation of NAN and AAN by (i) measuring both together as described by the present invention and, (ii) measuring AAN above, in the absence of the matrix which converts NAN to AAN.

The process of this invention can be practiced with a variety of analytes, a variety of monoclonal and polyclonal antibodies cross-reactive to such analytes, labels such as radioactive, enzyme, flourescence etc., a variety of matrices, and a variety of solid-phases.

The process of this invention can be practiced to measure a family of analytes which contain a common labile group which gets similarly altered in the sample environment and on conjugation. Such is the case with the family of beta-lactam antibiotics.

The following detailed steps and examples are cited to demonstrate the utility of this invention but not to limit its application.

STEP I

Preparation of Immunogen (CAAN) Exemplified by Formation and Purification Penicilloyl Derivative of Rabbit Serum Albumin (RSA)

Native Analyte-Benzylpenicillin (Penicillin-G) (PEN) was covalently conjugated to rabbit serum albumin (RSA) through the beta-lactam ring of the penicillin molecule and the epsilon-amino groups of proteins according to published procedures (Brown et al, U.S. Pat. No. 4,347,312 (1982) and Wal, J. M. et al, FEBS Letters 57, Pages 9-13 (1978)) and described below.

1.6 g of RSA was placed in a minimum volume sodium carbonate buffer at a pH of 10.4 and temperature of 4° C. to which 2.0 g of penicillin-G (PEN) was added and the pH adjusted to 9.6. After 16 hours, an additional 0.75 g PEN was added, the temperature being maintained at 4° C. Eight hours later, another 0.75 g PEN was added. Twelve hours later the mixture was eluted through a Sephadex G-200 column. After elution, cysteine hydrochloride was added to give a concentration of 0.1 molar and the pH was adjusted to 7.5. The mixture was then incubated at 37° C. for 1 hour. Thereafter, the mixture was again eluted through a Sephadex G-200 column, washed with water and the resulting PEN-RSA conjugate lyophilized for storage until ready for further use. An alternative method is next described.

To a solution of 100 mg of dried and electrophoretically pure RSA in 1 ml of 1M carbonate buffer pH 10.4, 1.2 g of penicillin G (crystallized sodium benzyl penicillinate, Specia) is added. After 12 hours of contact at +4° C. 600 mg of penicillin is added. 12 hours later, 600 mg of penicillin is again added. The molar concentration of penicillin is then about 500 times greater than the available-WH2 group concentration. After a total of 30-36 hours of incubation at +4° C., the reaction mixture is put on a Sephadex column G25 (K26/40-Pharmacia) equilibrated with 0.15M NaCl in 0.01M phosphate buffer (pH 7.4). Elution is done with the same buffer at laboratory temperature. Fractions of 0.5 ml are recovered and tested by ultraviolet spectroscopy at 280 nm. The penicilloyl-RSA conjugate is thus entirely separated from the excess free penicillin.

STEP II

Preparation of Immunogen (CAAN) Exemplified by Formation and Purification Penicilloyl Derivative of Bovine Gamma Globulin (BgG)

The immunogen is obtained by coupling native analyte penicillin to bovine gammaglobulins (BGG), a penicillin-protein conjugate being formed. The conjugation reaction, involving the formation of covalent bond between penicilloyl groups and available epsilon-amino groups of BGG (Wal, J. M. et al, FEBS Letters 57, Pages 9-13 (1975)) as described below.

Preparation and Purification of Conjugate

To a solution of 100 mg of dried and electrophoretically pure BGG (Boehringwerke A. G.) in 1 ml of 1M carbonate buffer pH 10.4, 1.2 g of penicillin G (crystallized sodium benzyl penicillinate, Specia) is added. After 12 hours of contact at +4° C. 600 mg of penicillin is added. 12 hours later 600 mg of penicillin is again added. The molar concentration of penicillin is then about 500 times greater than the available —NH2 group concentration. After a total of 30-36 hours of incubation at +4° C., the reaction mixture is put on a Sephadex column G25 (K26/40 —Pharmacia) equilibrated with 0.15M NaCl in 0.01M phosphate buffer (pH7.4). Elution is done with the same buffer at laboratory temperature. Fractions of 0.5 ml are recovered and tested by ultraviolet spectroscopy at 280 nm. The penicilloyl-BGG conjugate is thus entirely separated from the excess free penicillin. An alternative method is next described.

1.6 g of bovine gamma globulin was placed in a minimum volume sodium carbonate buffer at a pH of 10.4 and temperature of 4° C. to which 2.0 g of penicillin-G (PEN) was added and the pH adjusted to 9.6. After 16 hours, an additional 0.75 g PEN was added, the temperature being maintained at 4° C. Eight hours later, another 0.75 g PEN was added. Twelve hours later the mixture was eluted through a Sephadex G-200 column. After elution, cysteine hydrochloride was added to give a concentration of 0.1 molar and the pH was adjusted to 7.5. The mixture was then incubated at 37° C. for 1 hour. Thereafter, the mixture was again eluted through a Sephadex G-200 column, washed with water and the resulting PEN-BGG conjugate lyophilized for storage until ready for further use.

STEP III

Preparation of Antibodies (Ab (AAN)) Exemplified by Formation of Rabbit Anti-Pen.BgG Antibodies to penicillin were raised in rabbits by injecting immunogen (PEN-BGG), dissolved in saline and emulsified 50:50 with Freund's complete adjuvant, subcutaneously at ten day intervals. Serum was collected and held at −10° C. until needed.

STEP IV

Preparation of Antibodies (Ab (AAN)) Exemplified by Goat Anti-Pen.BgG

Antibodies to Pen.BgG raised in goat were purchased from Biolac, Logan, Utah.

STEP V

Purification of Rabbit Antibody (a) Immunosorbent Procedure

Insolubilization of BGG. BGG 250 mg was dissolved in 5 ml of 0.1M phosphate buffer pH 7. While the solution was stirred at room temperature, 1 ml of a 2.5 per cent aqueous solution of glutaraldehyde was added dropwise. A gel was formed almost instantaneously, and this was allowed to stand for 3 hour at room temperature.

Five hundred mg of the insolubilized protein were dispersed in 200 ml of 0.2M phosphate buffer pH 7.2–7.4 and homogenized by little portions, in a loose fitting Potter homogenizer. The resulting suspension was centrifuged for 15 min at 3,000 rpm and +4° C. The whole operation of homogenization and centrifugation was repeated two or three times. The insoluble protein was suspended in 200 ml of the eluting fluid to be used (0.1M glycine-HCl) buffer pH 2.8 and centrifuged. This operation was repeated once more. The immunoabsorbent was then washed by centrifugation with phosphate buffer until the supernatant had an optical density of 0 at 280 nm (generally after two washings).

To employ the immunoabsorbent, appropriate volumes of whole immune serum were mixed in centrifuge tubes with the insoluble protein. The mixture was stirred gently for 30 min at room temperature and then centrifuged (3,000 rpm, 15 min, +4° C.). The supernatant was kept in order to measure non-absorbed antibodies. The precipitate was suspended in buffered physiological saline (PBS) 3–4 times the volume of the antiserum added, and centrifuged as above. Washing with PBS was continued (about 3–4 times) until the supernatant had an optical density of less than 0.040 at 280 nm. To elute absorbed proteins 0.1M glycine-HC buffer pH 2.8 was used. The immunosorbent was suspended in a small volume, stirred with a magnetic stirrer for 5 min at room temperature and then centrifuged at 10,000 rpm for 15 min. This step was repeated twice. The supernatants were filtered and dialysed against several changes of cold saline.

STEP VI

Purification of Goat or Rabbit Anti-Pen.BgG

Glass beads having a suitable surface for bonding the conjugate may be prepared by:

a. silanizing and succinylating the glass beads to provide a succinamidopropyl-surface;

b. converting the succinamidopropyl-surface to the acyl chloride derivative by treatment under anhydrous conditions.

c. reacting the acyl chloride derivative with either 3-mercaptopropinic acid or mercaptoacetic acid under anhydrous conditions whereby the surface of the glass beads is activated; and d. drying the activated glass beads.

The silanizing and succinylating is carried out according to known procedures. Thus, silanizing is accomplished generally by treating the inorganic metal oxide material with an aqueous solution (e.g., about 10%) of the triethoxyaminopropylsilane at a pH of about 4. Thereafter, succinylating is accomplished by treating the material with either an aqueous solution of succinic anhydride at a pH of about 6, or an aqueous solution of succinic acid and carbodiimide.

Formation of the acyl derivative is accomplished by reaction with thionyl chloride dissolved in an inert organic solvent (e.g., methylene chloride) in the absence of water, i.e., under anhydrous conditions. At this point, the acyl derivative is reacted with either mercaptopropionic acid or mercaptoacetic acid dissolved in an inert organic solvent such as methylene chloride in the absence of water. Upon completion of the reaction, the material is dried, in vacuo, and stored until ready for use.

Immobilization of the Pen.RSA conjugate is accomplished by simply adding a solution of the conjugate at a pH around neutrality (e.g., 5 to 8) to a solid matrix (e.g., dry glass beads).

The antiserum was then purified by passing through columns of these beads and the columns thoroughly washed with physiologically buffered saline solution (PBS) then eluted with 0.1M acetic acid. The eluent was mixed immediately with pH 10, 0.1M sodium bicarbonate to neutralize the acid.

STEP VII

Signal Generating Molecule from AAN Exemplified by Radioiodination of Penicillin RSA 125I penicillin RSA was prepared by reacting 20 ul of 1 mg/ml penicillin RSA with 1 mCi of 125INa and 10 ul of chloramine T. The reaction was stopped by adding sodium metabisulfite. The reaction product was separated on a column and active fractions were used.

STEP VIII

Signal Generating Molecule (AAN*)—Horseradish Peroxidase (HRP) Conjugate of Penicillin Penicillin was linked to HRP by using an amide linkage using a carbodiimide carboylactivating reagent.

STEP IX

Signal Generating Molecule (AAN*) Horseradish Peroxidase Conjugate of Pen.RSA

Periodate method of conjugating HRP with protein was used to conjugate HRP to Pen.RSA made according to Step 1.

STEP X

Signal Generating Antibody—(Ab (AAN*))—Alkaline Phosphate Conjugate of Anti-Penicilloyl Antibodies Antibodies purified according to Step VI were conjugated to alkaline phosphatase by the gluteraldehyde method. Similarly, purified antibodies can also be conjugated to horseradish peroxidase.

EXAMPLE I

Conversion of NAN to AAN Examplified by Conversion of Native Penicillin to Penicilloyl Group Derivative During Test Procedure Antibody raised against penicillin BGG was used to study the conversion of penicillin to penicilloyl derivative under alkaline conditions in milk and in water.

Rabbit anti-penicillin BGG (1:500 dilution) was immobilized on nylon beads coupled with goat anti-rabbit IgG antibodies. Penicillin was added to milk and water to achieve a level of 0.012 ppm. One hundred micro liters of penicillin solution (water or milk) was reacted with immobilized anti-penicillin.BgG and sequentially with 125I penicillin.RSA (100 ul) for incubation periods of 60 minutes. It was found that binding of penicillin.RSA was inhibited only when formation of penicilloyl derivatives occurred through reaction of milk proteins with penicillin at high pH.

Ratio of Bound Counts with Penicillin/Bound Counts without penicillin × 100 is given below:

| Condition | Water | Milk |
|---|---|---|
| pH 6.8 | 89.7 | 100 |
| pH 10.4 | 110.7 | 69.3 |

This suggested that at pH 6.8 and in the absence of proteins, the presence of cold penicillin had very little inhibition on reaction of the antibody and labelled penicillin RSA. However, in the presence of milk protein and high pH, condition under which native penicillin became altered by the opening of its beta-lactam ring one obtains significant inhibition.

EXAMPLE II

Conversion of NAN-AAN Exemplified by Native Penicillin to Penicilloyl Group Derivative During Test Procedure The same method as Example I was repeated with differing amounts of penicillin being added to milk at various pH levels.

The ratio of Bound counts with penicillin/Bound counts without penicillin × 100 was determined:

| Penicillin Concentration | pH = 6.7 | pH = 10.0 |
|---|---|---|
| 0.003 ppm | 97 | 60 |
| .006 | 98 | 52 |
| .012 | 93 | 47 |
| .024 | 98 | 41 |
| .048 | 92 | 35 |
| .096 | 82 | 29 |

The data shows that conversion of native penicillin to penicilloyl derivative increases the inhibition and penicillin becomes measurable.

EXAMPLE III

Demonstration of Competitive Test Examplified by Fast Assay to Detect Penicillin in Milk 200 ul penicillin HRP conjugate was diluted 1:25 in Tris buffer with 10% polyethylene glycol. Milk containing various amounts of penicillin (300 ul) was placed with 100 ul of 0.2N NaOH containing 3% polyethylene glycol in contact with anti-penicillin BGG coated 8 mm polystyrene beads in 12×75 antibody coated plastic tubes. The reaction was carried out for 10 minutes. The tubes were washed three times and 200 ul ortho phenylenediamine-H2O2 mixture was added. The intensity at 490 nm of color was as follows after 5 minutes.

| Sample | O.D. |
|---|---|
| No penicillin | 2.6 |
| 0.01 ppm penicillin | 2.6 |
| 0.1 ppm penicillin | 2.3 |
| 1 ppm penicillin | 1.3 |

The data shows that small amounts of penicillin could be rapidly detected through the use of the proposed invention.

EXAMPLE IV

Demonstration of A Competitive Test Exemplified by Fast Assay to Detect Penicillin in Milk This test was similar to the previous Example III except HRP conjugate of penicillin RSA was used. The conjugate was diluted 1:25 in Tris, 10% PEG. 100 ul of Tris was reacted with 300 ul milk, 100 ul 0.2N NAOH, 3% PEG in antibody coated tubes with antibody coated plastic bead for 10 minutes. After three washing OPD-H2O2 mixture was added. The following color densities were found:

| Sample | O.D. |
|---|---|
| Milk | 2.2 |
| 0.01 ppm penicillin | 2.0 |
| 0.1 ppm penicillin | 1.4 |

The test data shows that Pen.RSA conjugate could be used instead of penicillin conjugation.

EXAMPLE V

Demonstration of Test Exemplified by Use of Immunometric Technique

Polystyrene beads were coated with Pen.RSA. Alkaline phosphatase anti-penicillin antibody conjugate made per Step X was used. Tube containing coated bead was incubated with 300 ul milk, 100 ul of 0.2 n NaOH and 100 ul of conjugate (1:10 dilution) for 10 minutes. Tubes were washed three times with water and 250 ul of P-nitrophenyl phosphate was added and color density was read after 15 minutes.

| Sample | O.D. |
| --- | --- |
| No penicillin | 1.94 |
| .001 ppm penicillin | 1.75 |
| .01 ppm penicillin | 1.70 |
| .1 ppm penicillin | 1.28 |

The test data shows that a labelled antibody could be used for the test.

EXAMPLE VI

Demonstration of Test—Use of Sequential Technique

Polystyrene beads and tube were coated with purified antibodies made per Step VI. HRP penicillin conjugate made per Step VIII was used. 200 ul of milk containing various amounts of penicillin was incubated for 10 minutes in coated test tube containing coated beads and 100 ul of 0.1N NaOH, 3% PEG. After incubation, tubes were washed three times with 2 ml buffer 100 ul of HRP penicillin. Conjugate was added and incubation for 10 minutes. After 3 washed 200 ul of OPD H202 was added and color density was read after 10 minutes.

| Sample | O.D. |
| --- | --- |
| No penicillin | 2.01 |
| .001 ppm penicillin | 1.99 |
| .01 ppm penicillin | 1.85 |
| .1 ppm penicillin | 1.46 |

The test results show the use of the sequential assay technique.

EXAMPLE VII

Demonstration of Test—Use of Biochemical (Enzyme)

Polystyrene beads were coated with Pen.RSA. HRP anti-penicillin antibody conjugate made per Step X was used. 250 ul of milk containing various amounts of penicillin was incubated for 10 minutes in a tube containing a coated bead and 150 ul of solution containing enzyme (lactamase), 0.2 m EDTA, 10% peg and HRP conjugated antibodies. Tubes were washed three times with buffer after the incubation period. 250 ul of OPD-H202 was added and color density was read after 5 minutes.

| Sample | O.D. |
| --- | --- |
| No penicillin | 1.44 |
| 0.01 ppm penicillin | 1.01 |
| 0.1 ppm penicillin | 0.67 |

The test results show the use of a biochemical agent for the detection of penicillin.

Whereas the preferred embodiment of the present invention has been described above, it is contemplated that other alterations and modifications may become apparent to those skilled in the art having read the above disclosure. Such modifications may include attaching the label to different molecules, the use of monoclonal antibodies, and utilizing various techniques of differentiating a bound fraction from an unbound fraction. Modifications may also include methods for altering a native molecule through chemical, biochemical or physical methods, and methods whereby a family of the analyte consisting of a common labile molecular form is measured through the use of one or more antibodies. It is therefore intended that the appended claims be interpreted as covering all such alterations and modifications as fall within the true spirit and scope of the invention.

What is claimed is:

1. A method for quantitating a beta-lactam antibiotic in a sample, said beta-lactam antibiotic being present in said sample in a closed ring form and an open ring derivative thereof, said method comprising:
   a. combining an antibody specific for said open ring derivative of said antibiotic and said sample in a reaction matrix that converts said closed ring form to said open ring form and produces a conjugate of said open ring form; and
   b. measuring the amount of antibody binding to determine the amount of said beta-lactam antibiotic present in said sample.

2. The method of claim 1 wherein said sample contains protein.

3. The method of claim 1 wherein said open ring derivative is produced by exposing said antibiotic to a high pH; in the reaction matrix.

4. The method of claim 1 wherein said open ring derivative is produced by exposing said antibiotic to a beta-lactamase enzyme in the reaction matrix.

5. A method for quantitating a beta-lactam antibiotic in a protein-containing sample, said beta-lactam antibiotic being present in said sample in a closed ring form and an open ring derivative thereof, said method comprising:
   a. combining an antibody specific for said open ring derivative of said antibiotic and said sample in a reaction matrix that converts said closed ring form to said open ring form and produces a conjugate of said open ring form, said reaction matrix having a high pH; and
   b. measuring the amount of antibody binding to determine the amount of said beta-lactam antibiotic present in said sample.

6. The method of claim 5 wherein said sample is milk.

7. The method of claim 5 wherein said beta-lactam antibiotic is a penicillin.

8. The method of claim 5 wherein said pH is about 10.

9. The method of claim 5 wherein said method is a competitive immunoassay technique.

10. The method of claim 9 wherein:
    a. said antibody is affixed to a solid phase;
    b. labeled conjugate comprising said open ring derivative of said antibiotic is present in said reaction matrix; and
    c. the amount of antibody binding is determined by detecting the amount of solid phase-affixed label.

11. The method of claim 5 wherein said method is a sequential immunoassay technique.

12. The method of claim 11 wherein:
    a. said antibody is affixed to a solid phase;
    b. said sample is mixed with said antibody prior to addition of labeled conjugate comprising open ring derivative of said antibiotic; and
    c. the amount of antibody binding is determined by detecting the amount of solid phase-affixed label.

13. The method of claim 5 wherein said method is an immunometric immunoassay technique.

14. The method of claim 13 wherein:

a. conjugate comprising open ring derivative of said antibiotic is affixed to a solid phase;
b. said antibody is labeled; and
c. the amount of antibody binding is determined by detecting the amount of solid phase-affixed label.

15. A method for quantitating a beta-lactam antibiotic in a protein-containing sample, said beta-lactam antibiotic being present in said sample in a closed ring form and an open ring derivative thereof, said method comprising:

a. combining a solid phase-affixed conjugate comprising open ring derivative of said antibiotic, an antibody specific for said open ring derivative of said antibiotic and said sample in a reaction matrix that converts said closed ring form to said open ring form and produces a conjugate of said open ring form, said reaction matrix containing a beta-lactamase enzyme;
b. measuring the amount of solid phase-affixed antibody to determine the amount of said beta-lactam antibiotic present in said sample.

16. The method of claim 15 wherein said antibody is labeled.

17. The method of claim 15 wherein said sample is milk.

18. The method of claim 15 wherein said beta-lactam antibiotic is a penicillin.

* * * * *